United States Patent [19]

Kaplan

[11] 4,408,988
[45] Oct. 11, 1983

[54] ORTHODONTIC APPLIANCE

[76] Inventor: Laurie M. Kaplan, 10 Monroe Blvd., Long Beach, N.Y. 11561

[21] Appl. No.: 416,484

[22] Filed: Sep. 10, 1982

[51] Int. Cl.³ .............................................. A61C 7/00
[52] U.S. Cl. .................................................... 433/3
[58] Field of Search .................................. 433/2, 3, 4

[56] References Cited

U.S. PATENT DOCUMENTS 2,643,908  6/1953  Grinnell .................................. 433/3

Primary Examiner—Robert Peshock
Attorney, Agent, or Firm—Frank P. Cyr

[57] ABSTRACT

An orthodontic appliance designed specifically for use by a dentist or dental assistant in placing the cut ends of a ligature wire under the arch wire employed in the formation of a tooth corrective arrangement commonly known as "braces". The appliance comprises a finger mounted tool formed of metal plastic or any other suitable material and is adapted to be fitted over a finger or thumb of the user and is provided with a notched-out area and serrations to assist in guiding the wire ends under the arch wire.

1 Claim, 11 Drawing Figures

ORTHODONTIC APPLIANCE

BACKGROUND OF THE INVENTION

The common orthodontic appliance usually employs metal bands which are adapted to encircle the teeth and which form a surface to which a bracket may be secured as by any known means and to thereafter secure a ligature wire to the bracket. Normally the ends of such ligature wire are twisted using a proper tool for this purpose and then the twisted ends are cut. The ligature wire is an extremely thin wire and when the twisted ends of the wire are cut, the cut wires must then be safely placed behind the arch wire where it will be kept, thus avoiding injury to the wearer of the corrective appliance. Unless the cut twisted ends of the wire are placed or tucked under the arch wire, the cut ends of the wire can cause damage to the interior of the mouth of the wearer of the corrective appliance.

With the above in mind, it is one object of the invention to provide an inexpensive yet effective appliance which may be readily adapted to a finger or thumb of the user and which will engage the twisted end of the ligature and guide the same under the arch wire.

Another object of the invention is to provide a finger or thumb held appliance which can be adjusted to fit differently sized fingers or thumb and of such dimensions so as not to interfere with free movement of the first joint of the finger to which it is applied for use.

Another object of the invention is to provide the finger or thumb held appliance with a notch and/or serrations along the front of the appliance which will assist in engaging the cut twisted ends of a ligature wire and to guide the same for placement under the arch wire.

These and other objects and advantages attained by the invention will become more fully apparent as the following description is read in conjunction with the accompanying drawings.

DESCRIPTION OF THE PREFERRED EMBODIMENTS

Figure 1:
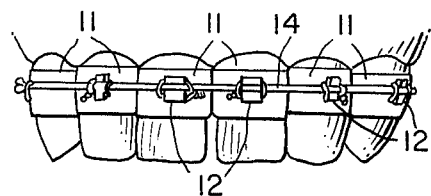
FIG. 1 is a front elevation showing an orthodontic appliance mounted on the teeth of a wearer.
Figure 2:
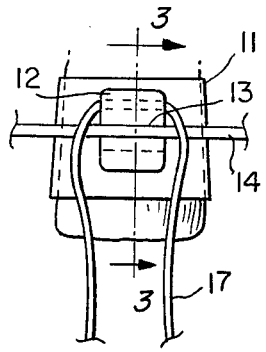
FIG. 2 is an enlarged view showing one tooth with a band and bracket secured thereto and disclosing the first step in securing a ligature wire to a bracket.

Referring now to the drawings wherein like reference numerals are employed to designate like parts throughout the several views, reference numeral 10 designates in general, the appliance of the present invention.

Before undertaking a description of the appliance of the present invention, it is thought best to illustrate the environment in which the same is used. Referring now to FIGS. 1 through 5, there is shown an orthodontic appliance applied to the teeth of the wearer for corrective purposes. A band 11 of metal, plastic or the like is first applied and secured in any known manner to each of the teeth over which will extend an arch wire employed in the corrective process for the teeth. Mounted on each of the bands 11 is a bracket 12 constructed of metal, plastic or other suitable material and the same is affixed to the band in any known manner as by adhesive or the like. As shown more clearly in FIG. 3 of the drawings, the bracket has a slot 13 extending throughout the width of the bracket and the arch wire 14 is disposed within the said slot.

Figure 3:
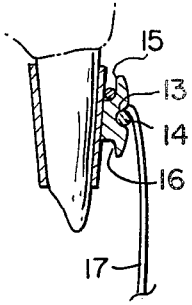
FIG. 3 is a section taken on lines 3—3 of FIG. 2, looking in the direction of the arrows.
Figure 4:
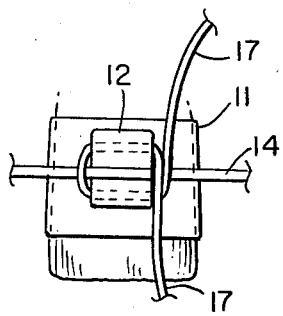
FIG. 4 shows the second step in securing a ligature wire to a bracket.

The bracket 12 as shown more particularly in FIG. 3 of the drawing comprises a wing-like structure with recesses 15, 16 formed rearwardly of the bracket and a ligature wire 17 extends in the recessed areas 15, 16 as shown more particularly in FIG. 4 of the drawings. Following the placement of the ligature wire in the aforesaid recessed areas of the bracket, the ligature wire is then twisted such as shown at 18 in FIG. 5 of the drawings. Following the twisting of the ends of the ligature wire, the same is cut as at 19 using a suitable instrument to effect the cut. After the wire has been cut, the ends of the twisted wires are then tucked under the arch wire 14 such as shown in FIG. 6 of the drawings.

Shown in FIGS. 1 to 6 inclusive of the drawings, is one manner in which the band and bracket are mounted on a tooth. Other manners of securing the band and bracket may be employed and the structure shown in FIGS. 1 to 5 inclusive of the drawings is to be considered as illustrative only and not restrictive to the present invention which will now be discussed in detail.

The appliance of the present invention comprises a finger or thumb mounted appliance 20 which is to be employed to tuck the ends of the twisted wire under the arch wire. The appliance comprises a pair of finger or thumb encircling bands 21, 22 formed of any suitable material. However, in order for the appliance to properly fit on the finger or thumb of the user, the bands are preferably formed of a resilient metal or plastic so as to enable the bands to firmly yet comfortably fit the finger or thumb of the user.

Figure 7:
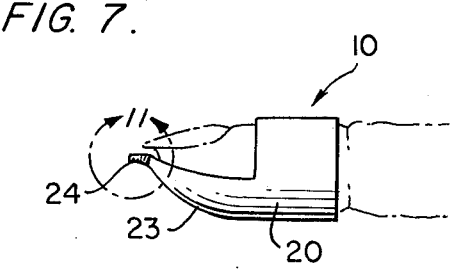
FIG. 7 is a side elevation showing the appliance positioned on the finger of the user.
Figure 8:
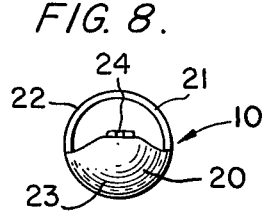
FIG. 8 is a front elevation of the appliance.
Figure 9:
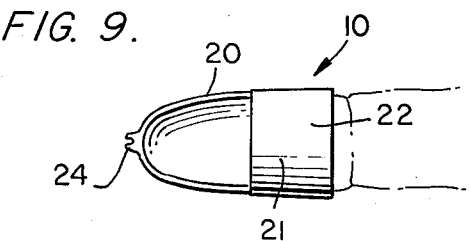
FIG. 9 is a top plan view of the appliance again as applied to the finger of the user of the appliance.
Figure 10:
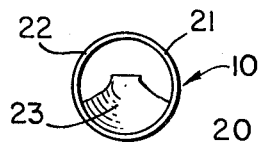
FIG. 10 is a rear view of the appliance.
Figure 11:
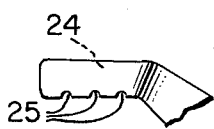
FIG. 11 is an enlarged view taken by the circled portion 11 of FIG. 7.

As shown more particularly in FIGS. 7 and 8 of the drawings, the forward portion of the appliance is curved as at 23 so as to conform to the curvature of the finger or thumb and terminates at the forward edge thereof in a notch 24 and serrations 25 for a purpose to be more fully described hereinafter.

As shown in the drawings, the appliance is so constructed as not to overlie the first joint of the finger or thumb, thus enabling the user thereof to freely bend the finger or thumb during the use of the appliance.

Figure 5:
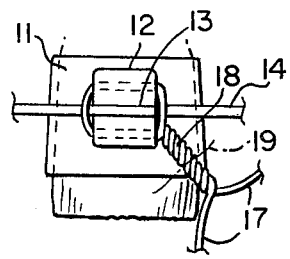
FIG. 5 shows the third step in applying the ligature wire to a bracket.
Figure 6:
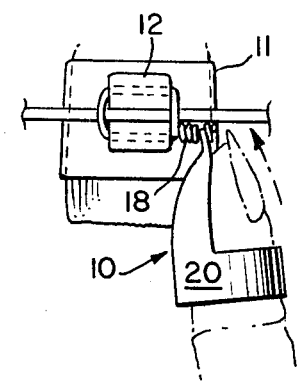
FIG. 6 shows the manner in which the appliance of the present invention is employed to tuck the cut ends of the twisted ligature wire under the arch wire.

As explained previously, following the application of the ligature wire to the bracket and the ends of the twisted wire cut-off, the user of the appliance then places the appliance over the finger or thumb and then engages the twisted wires with the notch 24 and then proceeds to tuck the twisted wire ends under the arch wire in the manner illustrated in FIG. 5 of the drawings. The placement of the twisted wire ends under the arch wire will thus prevent the wire ends to be exposed in the mouth of the wearer of the orthodontic appliance thereby preventing injury to the wearer of the orthodontic appliance. The serrations 25 provided at the front end of the appliance may also be employed to engage with the twisted wire ends to assist in tucking the same under the arch wire.

As stated previously, the orthodontic appliance shown in FIGS. 1 to 5 inclusive of the drawings is but one manner of securing arch and ligature wires to teeth to be subjected to a corrective action and as can be appreciated, the appliance of the present invention can be as effectively employed in tucking the ends of the ligature wire under an arch wire in instances where a different type of orthodontic appliance is employed for effecting a corrective action to the wearer of the orthodontic appliance. Suffice to say that the appliance of the present invention can be effectively used whenever a twisted ligature wire is to be tucked under an arch wire.

While I have described a preferred form of the invention, it is to be understood various changes and modifications are possible without departing from the spirit of the invention.

I claim:

1. An appliance for tucking the ends of twisted wire ends of a ligature wire under an arch wire employed in an orthodontic apparatus, said appliance comprising a finger or thumb mounted structure having a pair of resilient bands engaging a finger or thumb of the user and substantially encircling the same forwardly of the first joint of the said finger or thumb said structure provided with a concave portion at the forward end of said appliance conforming to the convex surface of the first joint of the said finger or thumb of the user of the a flattened portion extending beyond said convex surface at the front end of said appliance, a centrally located notch formed at the forward end of said flattened portion and a plurality of serrations formed on the undersurfaces of said flattened portion, the notch and said serrations formed centrally of said flattened portion for engaging with the twisted wire ends of said wire for tucking the twisted ends of said wire under an arch wire employed in an orthodontic appliance.

* * * * *